(12) United States Patent
Gillis et al.

(10) Patent No.: US 10,874,707 B2
(45) Date of Patent: Dec. 29, 2020

(54) ANTIOXIDANT ENRICHED DISTILLED ALCOHOL PRODUCT AND PROCESS THEREFOR

(71) Applicants: Alan B. Gillis, Springfield (CA); Judith M. Gillis, Springfield (CA)

(72) Inventors: Alan B. Gillis, Springfield (CA); Hyun Suk Lee, Springfield (CA); Judith M. Gillis, Springfield (CA); Rodney J. Gillis, Springfield (CA)

(73) Assignees: Alan B. Gillis, Springfield (CA); Judith M. Gillis, Springfield (CA)

( * ) Notice: Subject to any disclaimer, the term of this patent is extended or adjusted under 35 U.S.C. 154(b) by 837 days.

(21) Appl. No.: 15/279,952

(22) Filed: Sep. 29, 2016

(65) Prior Publication Data

US 2017/0014466 A1 Jan. 19, 2017

Related U.S. Application Data

(63) Continuation of application No. PCT/CA2015/050239, filed on Mar. 27, 2015.

(30) Foreign Application Priority Data

Apr. 3, 2014 (CA) .................................. 2847993

(51) Int. Cl.
| | | |
|---|---|---|
| *A61K 36/81* | (2006.01) | |
| *C12H 6/02* | (2019.01) | |
| *C12G 3/04* | (2019.01) | |
| *A61K 9/00* | (2006.01) | |
| *A61P 39/06* | (2006.01) | |

(52) U.S. Cl.
CPC ............ *A61K 36/81* (2013.01); *A61K 9/0095* (2013.01); *C12G 3/04* (2013.01); *C12H 6/02* (2019.02); *A61K 2236/00* (2013.01); *A61K 2236/10* (2013.01); *A61K 2236/33* (2013.01); *A61K 2236/39* (2013.01); *A61P 39/06* (2018.01)

(58) Field of Classification Search
CPC .. A61K 36/81; A61K 9/0095; A61K 2236/00; A61K 2236/10; A61K 2236/33; A61K 2236/39; C12H 6/02; C12H 3/04
See application file for complete search history.

(56) References Cited

U.S. PATENT DOCUMENTS

2005/0136141 A1 6/2005 Stoner et al.

OTHER PUBLICATIONS

Halpren J "Anti-Oxidanr Cocktail", Mar. 26, 2010, 1 page. (Year: 2010).*
Dumlu Mu, Gürkan E "Elemental and Nutritional Analysis of Punica granatum from Turkey" Journal of Medicinal Food, 10(2), Published Online Jul. 26, 2007, pp. 392-395 (abstract only); doi.org/10.1089/jmf.2006.295. (Year: 2007).*
Halpren J "Anti-Oxidant Cocktail", Mar. 26, 2010, 1 page. (Year: 2010).*
Nour, V. et al., Anthocyanins profile, total phenolics and antioxidant activity of black currant ethanolic extracts as influenced by genotype and ethanol concentration, Food Chem., Apr. 13, 2013, vol. 141, No. 2, pp. 961-966.
Nicoue, EE. et al., Anthocyanins in Wild Blueberries of Quebec: Extraction and Identification. J. Agric Food Chem., Jun. 19, 2007, vol. 55, No. 14, pp. 5626-5635.
Libran, CM. et al., Polyphenol extraction from grape wastes: Solvent and pH effect. Agr Sci., 2013, vol. 4, No. 9B, pp. 56-62.
Bridgers, EN. et al. Extraction of anthocyanins from industrial purple-fleshed sweetpotatoes and enzymatic hydrolosis of residues for fermentable sugers. Ind. Crops Prod., 2010, pp. 613-620.

* cited by examiner

*Primary Examiner* — Aaron J Kosar
(74) *Attorney, Agent, or Firm* — Standley Law Group LLP; Stephen L. Grant; Beverly A. Marsh

(57) ABSTRACT

A process for producing a distilled ethanol product comprising an antioxidant component and an ethanol component is described. In the process, plant matter containing antioxidants is washed, frozen and exposed to an input volume of ethanol. Antioxidants are ethanolically extracted from the frozen plant matter. The plant matter and the liquid ethanol fractions are then separated and the plant matter having antioxidants extracted therefrom is used to produce ethanol which is subsequently used to extract antioxidants from a second batch of plant matter. The ethanol fraction having antioxidants therein is stored or diluted for later use.

10 Claims, 1 Drawing Sheet

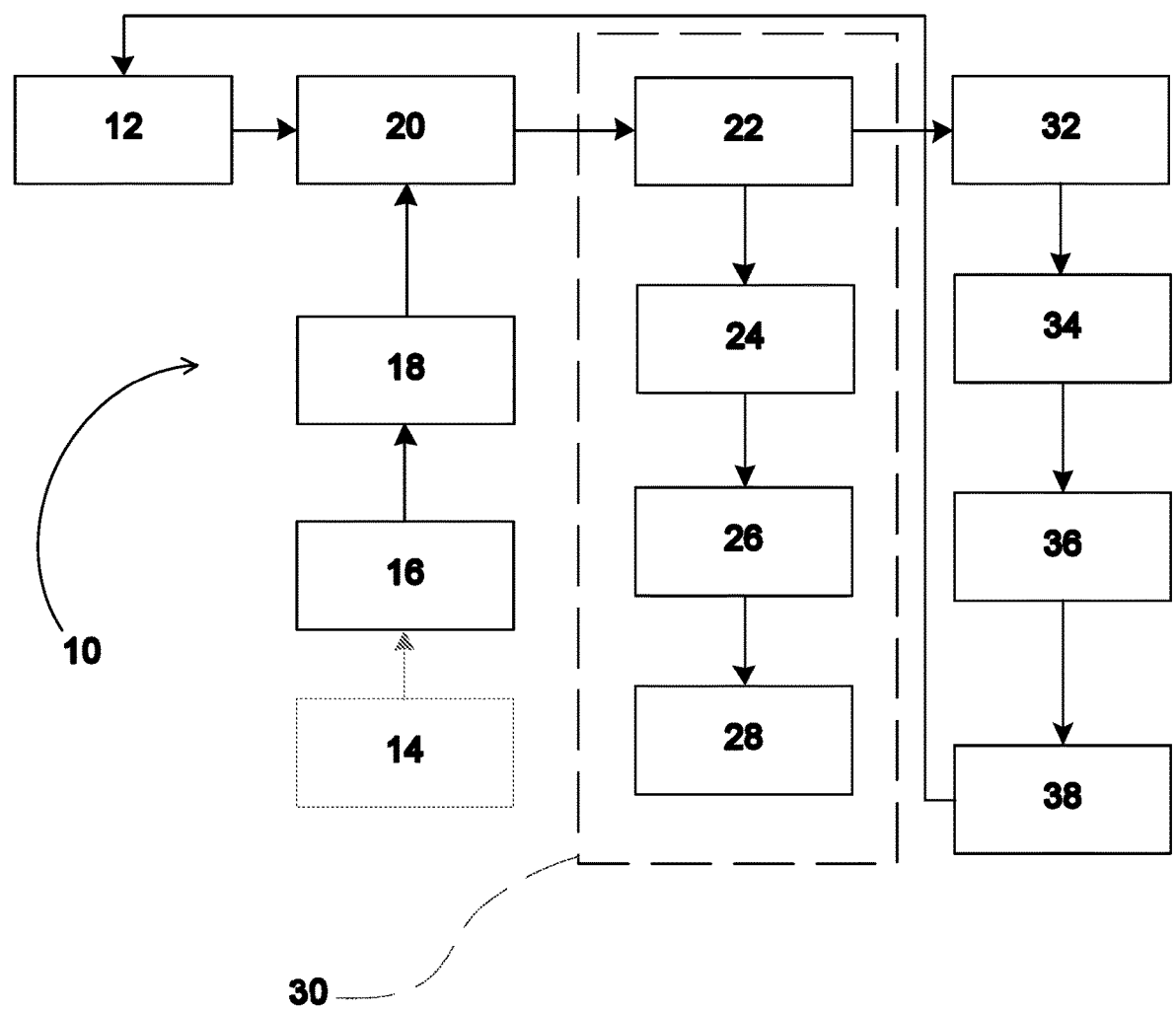

ANTIOXIDANT ENRICHED DISTILLED ALCOHOL PRODUCT AND PROCESS THEREFOR

RELATED APPLICATION

The present application is a U.S. Continuation application which claims benefit of priority to International Patent Application serial number PCT/CA2015/050239 entitled "Antioxidant Enriched Distilled Alcohol Product And Process Therefor", filed Mar. 27, 2015 which in turn claims benefit of priority to Canadian Patent Application serial number 2,847,993 entitled "Antioxidant Enriched Distilled Alcohol Product And Process Therefor", filed Apr. 3, 2014, the subject matter of each of which are herein incorporated by reference.

TECHNICAL FIELD

The present disclosure relates to distilled alcohol products and processes for producing distilled alcohol products containing antioxidants.

BACKGROUND

In recent years there has been an increasing desire among the public to consume functional foods and beverages as well as naturally-sourced compounds for alleviating or improving various medical ailments. A functional food can be broadly defined as a food which has an additional function, generally related to disease prevention and additional health-promoting attributes of a given food product. For example, a functional food is one that is natural or processed to contain known biologically-active compounds where such biologically-active compounds are known to provide a health benefit, such as aiding in the prevention or management of various ailments. Therefore, such foodstuffs can be considered to be fortified. Agriculture and Agri-Food Canada, for example, broadly defines a functional food as a food which is similar in appearance to, or may be, a conventional food that is consumed as part of one's diet, and that is demonstrated to have physiological benefits and/or reduce the risk of chronic disease beyond basic nutritional functions, i.e. they contain at least a certain bioactive compound.

Free radicals that contain oxygen are known as reactive oxygen species. Common reactive oxygen species, which occur as a result of chemical reactions in the body, are, for example, superoxide ($O^-_2$), Hydroxyl (OH.), Hydroperoxyl ($HO_{\cdot 2}$), Alkoxyl (LO. or RO.) and Peroxyl ($LO_2$. or $RO_2$.). Reactive oxygen species, in addition to being formed as part of oxidation reactions are crucial for life, are also known to be formed by exposure to substances such as smog, ozone, various chemicals, drugs, and radiation inter alia. When excessive reactive oxygen species chain reactions occur in a cell, they can cause damage or death to the cell. Antioxidants terminate these chain reactions by removing free radical intermediates, thus inhibiting further oxidation reactions.

From a nutritional perspective, an antioxidant functions, in one aspect, to dispose of reactive oxygen species in the body. Therefore, an antioxidant inhibits the oxidation of other molecules. Plants and animals maintain complex systems of multiple types of antioxidants, such as glutathione, vitamin C, vitamin A, and vitamin E as well as enzymes such as catalase, superoxide dismutase and various peroxidases. Reducing agents, such as thiols, ascorbic acid, or polyphenols can also be used to control the amount of reactive oxygen species in a given cell and thereby reduce oxidative stress that can cause damage to or kill cells. Accordingly, antioxidants are widely used in dietary supplements and have been investigated for the prevention of diseases such as cancer, coronary heart disease and other aliments.

Anthocyanins, polyphenol compounds belonging to the flavonoids class of molecules, are water-soluble vacuolar pigments that, depending on pH may appear red, purple, or blue. These are considered secondary metabolites when consumed by an individual since anthocyanins are metabolized to uric acid, which in turn increases the antioxidant capacity of blood.

Anthocyanins are known to occur in all tissues of higher plants including leaves, stems, roots, flowers and fruits and are particularly prevalent in plant matter with a rich blue or purple colour, such as blueberries. For example, plants rich in anthocyanins generally are from the *Vaccinium* genus, such as blueberry, cranberry, and bilberry; the *Rubus* genus, including black raspberry, red raspberry, blackberry, blackcurrant and cherry. Anthocyanins, although present, are less abundant in banana, asparagus, pea, fennel, pear, and potato.

Of particular interest are the Adirondack varieties of hybrid potatoes developed by Cornell University. These hybrid potatoes, which have blue flesh and skin with a slight purple tint (a red variety has a similar interesting appearance), contain high levels of anthocyanins. Accordingly, these red- and purple-fleshed hybrid potato varieties are a good source of antioxidants. However, certain drawbacks have been noted with the Adirondack potatoes from a commercial perspective. These potatoes tend to more readily suffer bruising as compared to traditional potato varieties. Therefore in a given quantity of Adirondack potatoes, there tend to be more 'B-grade' potatoes, which are generally rejected for sale for the purpose of eating. However, these B-grade potatoes can still be used for other purposes such as in the manufacture of alcohol.

Briefly, in the production of distilled alcohol, a mixture of milled grain or other fermentable carbohydrates such as from a fruit or vegetable is used. These fermentable carbohydrates, generally termed feedstock, are usually first cooked to gelatinize the starches and then enzymatically- or acid-treated to convert the carbohydrates into fermentable sugars in a process known as saccharification, which forms the mash. Following saccharification, yeast is added to the mash to ferment the sugars. At this point the mash is referred to as 'beer'. Here the sugars are converted to various alcohols by the yeast. A distillation process is then used which separates the various alcohols from the beer where ethanol is recovered, resulting in the recovery of the distilled alcohol—generally 95% ethanol. Therefore, following the distillation process, substantially pure ethanol is recovered which leaves behind a 'stillage' containing the higher boiling point components of the beer and any solids which may not have been previously filtered out of the beer. For example, ethanol has a boiling point of 78.5° C. in the anhydrous state and 78.15° C. when formed in the binary azeotrope with water. Therefore, an ethanol composition of about 95% ethanol can be distilled from the beer when heated to about 78° C. where the ethanol is evaporated and collected as a liquid by condensation of the ethanol vapour; thus separating and purifying the ethanol from the beer.

In the stillage, the beer remnants from the distillation process, and components such as fusel oils, remain. Fusel oils is a term used to describe higher alcohols, generally various ratios of propanol, butanol and amyl alcohol which are by-products of ethanol fermentation and have a higher boiling point than ethanol. Consumption of distilled alcohols having a degree of fusel oils therein is known to cause headaches and hangovers—such a distilled alcohol product may be considered to be a low-quality distilled alcohol product. It is believed that the fusel oils are primarily responsible for the headaches and hangovers of low quality distilled alcohol products.

This background information is provided to reveal information believed by the applicant to be of possible relevance. No admission is necessarily intended, nor should it be construed, that any of the preceding information constitutes prior art.

SUMMARY

The following presents a simplified summary of the general inventive concept(s) described herein to provide a basic understanding of some aspects of the invention. This summary is not an extensive overview of the invention. It is not intended to restrict key or critical elements of the invention or to delineate the scope of the invention beyond that which is explicitly or implicitly described by the following description and claims.

Briefly, it would be desirable to develop a process for producing distilled alcohol containing antioxidants. It has been observed that, although antioxidants may be present in the beer produced from antioxidant-rich plant matter for distillation, they are significantly removed as a result of the distillation process and are generally not present in the distilled ethanol product. One option is thus to reintroduce antioxidants recovered from the stillage into the distilled ethanol to produce a distilled antioxidant-containing ethanol product.

Processes have been attempted wherein the antioxidants are added back into the distilled alcohol product; however, the resultant antioxidant containing product is of a lower quality, and may exhibit "off flavors". In such processes, for example, using a potato beer made from Adirondack potatoes, the potato beer is distilled by conventional methods to produce ethanol, generally a 95% ethanol product for example. The 95% ethanol product in these methods is then diluted with the remaining stillage product so as to reintroduce the antioxidants to the distilled alcohol and reduce the ethanol content of the thus diluted antioxidant-containing product to about 40%. However, in such a process other undesirable compounds may also be reintroduced into the final product.

In order to address the potential issue of "off flavours" and lower quality products, the 40% ethanol product, or other percent dilution product, can then be further processed in order to produce a higher-quality product. For example, such lower-quality antioxidant containing ethanol products may be further processed by membrane purification to render a higher quality distilled antioxidant containing ethanol product. In another process, once the fermentation process has been completed, the beer may be sieved to remove solids and then be further processed by reverse osmosis to remove excess water and produce a concentrated ethanol product containing antioxidants. For example, the excess water may be removed so as to render an approximately 40% ethanol product which includes antioxidant phenol compounds. Both of these methods are time consuming and require the use of expensive equipment. Furthermore, although antioxidants may be conserved in the final product, these methods may not fully address the issue of purifying other components such as fusel oils out of the final product, which may lead to a lower-quality product.

Therefore it would also be desirable to develop a process to produce a distilled ethanol product containing antioxidants which is economical and which renders a higher-quality final product.

Briefly, in accordance with one embodiment of the instantly disclosed process, antioxidants are extracted from frozen and ground fruits, grains and/or vegetables using about 95% ethanol to produce an antioxidant-rich fluid. The remaining ethanol-washed fruit, grain and/or vegetable solids are cooked and pre-treated via saccharification, either by enzymes or acid or both, then fermented via yeast. The fermented mash is then distilled to generate about 95% ethanol to be invested in the extraction step of a next round of production of an antioxidant-rich fluid. Accordingly, the antioxidants are extracted from the frozen and cut or ground fruits, grain and/or vegetables using 95% ethanol produced in an earlier cycle.

In one aspect there is provided a process for producing an antioxidant containing distilled ethanol product. Accordingly there is also provided an antioxidant containing distilled ethanol product produced according to the process as defined herein. The process comprises freezing antioxidant containing plant matter, suitable for use in the production of ethanol, to render a frozen plant material. The frozen plant material is then subjected to a volume of a distilled input ethanol product so as to ethanolically extract antioxidants from the frozen plant material and render an antioxidant-rich ethanol fluid mixture having therein remnant solid plant matter. The remnant solid plant matter is then separated from the antioxidant-rich ethanol fluid mixture so as to obtain the antioxidant containing distilled ethanol product. A subsequent distilled ethanol product is then produced from the remnant solid plant matter.

In some embodiments, the subsequent distilled ethanol product is used as the distilled input ethanol product in a subsequent cycle for producing a further antioxidant containing distilled ethanol product.

In some embodiments, the distilled input ethanol product has an ethanol concentration of from about 70% to about 99% and in preferred embodiments, the distilled input ethanol product has an ethanol concentration of about 95%.

In some embodiments, the frozen plant material is further sliced or ground to reduce the size thereof and increase the surface area exposed to the distilled input ethanol product during antioxidant extraction.

In some embodiments, the antioxidant containing distilled ethanol product is further diluted to reduce the ethanol concentration thereof. For example, in some embodiments, the antioxidant containing distilled ethanol product is further diluted to reduce the ethanol concentration thereof to a concentration of from about 20% to about 69%. In preferred embodiments, the antioxidant containing distilled ethanol product is further diluted to reduce the ethanol concentration thereof to about 40%.

In some embodiments, the plant matter suitable for use in the production of ethanol is from the *Vaccinium* genus, *Rubus* genus, blueberry, cranberry, bilberry, black raspberry, red raspberry, blackberry, blackcurrant, cherry, banana, asparagus, pea, fennel, pear, or potato. In preferred embodiments, the plant suitable for use in the production of ethanol is Adirondack Blue potatoes or Adirondack Red potatoes.

In some embodiments, the frozen plant material and the distilled input ethanol product are provided for the ethanolic antioxidant extraction in a ratio between of from about 0.4 kg frozen plant material to about 1 liter ethanol and about 0.6 kg frozen plant material to about 1 liter ethanol. In preferred embodiments, the frozen plant material and the distilled input ethanol product are provided for the ethanolic antioxidant extraction in a ratio of from about 0.5 kg frozen plant material to about 1 liter ethanol.

In some embodiments, the pH of the distilled input ethanol product is adjusted so as to be in the range of from about 3.0 to about 6.0. In preferred embodiments, the pH of the distilled input ethanol product is adjusted so as to be about 4.5.

In some embodiments, during the ethanolic antioxidant extraction the frozen plant material and the distilled input ethanol product are maintained at a temperature of from about 10° C. to about 20° C. Preferably, during the ethanolic antioxidant extraction the frozen plant material and the distilled input ethanol product are maintained at a temperature of about 14° C. Furthermore, in some embodiments, the ethanolic antioxidant extraction proceeds for a time period of from about 1 minute to about 100 minutes and in preferred embodiments, the ethanolic antioxidant extraction proceeds for a time period of about 30 minutes.

In some embodiments, following the ethanolic antioxidant extraction, the antioxidant-rich ethanol fluid is separated from the remnant solid plant matter and said antioxidant containing distilled ethanol product is obtained and maintained in an environment substantially devoid of oxygen. For example, in some embodiments, the environment substantially devoid of oxygen is provided by a closed system. Additionally, in some embodiments the environment is provided by a blanket of inert gas. For example, the inert gas may be nitrogen or argon.

In another aspect, a comestible antioxidant containing distilled ethanol product comprising at least an antioxidant component and an ethanol component is provided.

In some embodiments of the comestible antioxidant containing distilled ethanol product, the antioxidant component comprises anthocyanins.

In some embodiments of the comestible antioxidant containing distilled ethanol product, the ethanol is distilled from a beer using sugars derived from potatoes. In preferred embodiments, the potatoes are Adirondack Blue potatoes, Adirondack Red potatoes or a combination of Adirondack Blue potatoes and Adirondack Red potatoes.

In some embodiments of the comestible antioxidant containing distilled ethanol product, the antioxidants are ethanolically extracted from a first frozen plant matter batch using a first distilled input ethanol product to render an antioxidant-rich ethanol fluid mixture having therein remnant solid plant matter, the solid plant matter subsequently being separated from the antioxidant-rich ethanol fluid so as to yield said antioxidant containing distilled ethanol product. Furthermore, in some embodiments, the remnant solid plant matter is used to produce a second distilled input ethanol product which is used subsequently to ethanolically extract antioxidants from a second frozen plant matter batch.

In some embodiments of the antioxidant containing distilled ethanol product as disclosed herein, the distilled ethanol product has an antioxidant concentration of from about 150 ppm to about 200 ppm.

Other aims, objects, advantages and features of the invention will become more apparent upon reading of the following non-restrictive description of specific embodiments thereof, given by way of example only with reference to the following description and accompanying drawings.

BRIEF DESCRIPTION OF THE FIGURES

In order that the invention may be better understood, exemplary embodiments will now be described by way of example only, with references to the accompanying drawing, wherein:

FIG. 1 is a flow diagram generally outlining an exemplary process for producing an antioxidant containing distilled ethanol product in accordance with the instant disclosure.

DETAILED DESCRIPTION

With reference to the disclosure herein and the appended FIGURE, a process in accordance with various embodiments of the invention is described so as to provide an antioxidant containing distilled alcohol product.

With reference to the disclosure herein and FIG. 1, there is provided at 10 an exemplary process for producing an antioxidant containing distilled ethanol product in accordance with various embodiments of the instant disclosure.

A distilled input ethanol product 12 is provided. Generally, the input ethanol product 12 will be a 95% ethanol product, however other concentrations of ethanol may be utilized. For example, the concentration of the input ethanol product 12 may be from about 70% to about 99% pure ethanol, however other concentrations may also be utilized if desired. A consideration in selecting the concentration of the input ethanol product 12, in accordance with the instant disclosure, is the nature and quantity of impurities that may be present in the input ethanol product. For example, as noted above, impurities in the ethanol product may result in off-flavours of the final product. When ethanol is distilled, the impurities are generally distilled out, and therefore a 95% ethanol product is preferred, however, if the input ethanol product is generally free from impurities and composed of mainly pure water and ethanol, a lower concentration of ethanol may be used. Accordingly, in some embodiments, a 95% ethanol product diluted to a lesser concentration, for example a 40% ethanol concentration with water may also be used.

Plant matter containing antioxidants 14, for example anthocyanins, suitable for use in producing a mash and subsequent fermentation for distillation to ethanol is provided. As noted above, the plant matter may be, for example, but not limited to, from the *Vaccinium* genus such as blueberry, cranberry, and bilberry; or the *Rubus* genus including black raspberry, red raspberry, blackberry, blackcurrant and cherry. Other suitable sources of plant matter may be banana, asparagus, pea, fennel, pear, and potato. In some embodiments of the instant disclosure certain grains may also be suitable, such as, for example, Charcoal purple wheat, Red Fife wheat and yellow *Luteus* wheat as well as other grain varieties with a high polyphenol content. In accordance with the exemplary embodiment described below, sources of plant matter are potatoes and, in particular, the darkly pigmented potato varieties of the Adirondack Blue potato and the Adirondack Red potato. However, as indicated above, various other sources of plant matter may utilized in some embodiments. The plant matter is washed to remove surface contaminants and then frozen where any liquids present in the plant matter 14 are converted to a solid state thus providing a washed and frozen plant material 16. Antioxidants are generally most stable at low temperatures. It has been surprisingly discovered that freezing the plant matter 14 prior to the antioxidant extraction to produce an antioxidant-rich ethanol fluid 20 (discussed in more detail below) yields a higher antioxidant value in the antioxidant-rich fluid 20 resultant from the antioxidant extraction in the distilled input ethanol product 12. Therefore, antioxidants are extracted by ethanolic extraction from the washed and frozen plant material 16 using the distilled input ethanol product 12 to produce an antioxidant-rich fluid 20.

Returning to FIG. 1, the now washed and frozen plant material 16 is cut to increase the surface area of the plant matter at 18 which is then subsequently exposed to the input ethanol 12 to yield the antioxidant-rich ethanol fluid 20. For example, in the case of potatoes, the potatoes are sliced to increase the surface area exposed to the ethanol. For example, in preferred embodiments the potatoes are sliced to provide slices of less than about 5.0 mm. In some embodiments, the plant matter 14, such as certain fruits and grains, does not lend itself to slicing and therefore, in order to increase the surface area thereof for exposure to the ethanol, such plant matter 14 is ground to expose an increased surface area from which the antioxidants and/or anthocyanins will be extracted to form the antioxidant-rich ethanol fluid 20.

As noted above, the now sliced and/or ground frozen plant material is then exposed to the input ethanol 12 to render the antioxidant-rich ethanol fluid 20. Therefore, once the suitable fruit, grain and/or vegetable matter is suitably prepared, it is placed in ethanol for a period of time so as to undergo an ethanol extraction of antioxidants and/or anthocyanins. The amount of time that the plant material is exposed to the ethanol for extraction of the antioxidants and/or anthocyanins is dependent upon of the amount of antioxidants and/or anthocyanins present in the plant matter 14 as well as the amount of time required to achieve the desired antioxidants and/or anthocyanins concentration in the antioxidant-rich ethanol fluid 20. For example, in the case of the abovementioned Adirondack Blue and Red potatoes, the sliced and frozen potatoes may be exposed to the ethanol for a time period of about of from about 1 minute to about 100 minutes. In preferred embodiments, the ethanolic antioxidant extraction proceeds for a time period of about 30 minutes. The extraction time may also be varied according to the plant matter 14 used in order to also extract certain desirable flavours and/or colorings from the plant material which may be desirable in a final antioxidant containing distilled ethanol product 28. For example, if using blueberries to provide the antioxidants, one may wish to increase the extraction time so as to lend a blueberry flavouring and confer a certain colouring to the final antioxidant containing distilled ethanol product 28. Additionally, in some embodiments, the frozen plant material 16 is exposed to the distilled input ethanol product 12 in a ratio of between from about 0.4 kg to about 0.6 kg frozen plant material to about 1 liter ethanol and in preferred embodiments in a ratio of about 0.5 kg frozen plant material to about 1 liter of ethanol. However one of skill in the art will appreciate that such a ratio will be variable dependent on the amount of antioxidants and/or anthocyanins in the plant material and the desired extraction level.

Once the extraction to produce the antioxidant-rich ethanol fluid 20 has been allowed to proceed until the desired antioxidant levels have been obtained as well as any other desired and extractable flavouring notes, the now antioxidant-rich ethanol fluid 20 is filtered at step 22 to remove remnant solid plant matter 32, resulting in filtered liquids 24. In some embodiments, the remnant solid plant matter 32 may also be removed from the antioxidant-rich ethanol fluid 20 by means of centrifugation or other suitable means so as to obtain the filtered liquids 24. Accordingly, the antioxidant-rich ethanol fluid 20 is thus separated from the remnant solid plant matter 32 to obtain the filtered liquids 24 and thus the antioxidant-rich ethanol product 26. The filtered liquids 24 comprise ethanol and antioxidants and/or anthocyanins and other flavours and may be termed an antioxidant-rich ethanol product 26. In some embodiments, the filtered liquids 24 are recovered from the filtering step at 20 in a closed system. For example, such a closed system may be a physically closed system which is substantially devoid of oxygen (i.e. an anaerobic environment). Such a closed system may be desirable in some embodiments since antioxidants are known to be susceptible to oxidation. In other embodiments, the solids may be filtered from liquids under an inert gas such as nitrogen or argon to obtain the filtered liquids 24. The closed system or filtering under an inert gas is provided so as to not expose the antioxidant-rich ethanol product 26 to oxygen which may decrease the amount of effective antioxidants in the antioxidant-rich ethanol product 26.

While continuing with the antioxidant-rich ethanol product 26 in a system which substantially limits exposure to an oxygen containing environment, the antioxidant-rich ethanol product 26 may, in some embodiments, at this point in the process be further filtered so as to remove undesired components such as potato sediments (carbohydrates), protein haze, etc. and/or contained for later use in food and beverage products. With reference FIG. 1, in some embodiments, the antioxidant-rich ethanol product 26 may be further diluted with water or other suitable liquid to a desired alcohol concentration. For example, in the production of a final antioxidant containing distilled ethanol product 28, the antioxidant-rich ethanol product 26 may be diluted to obtain a final antioxidant containing distilled ethanol product 28 to be bottled for distribution. In some embodiments, for example, the antioxidant-rich ethanol product 26 may be diluted to obtain an alcohol concentration of from about 20% to about 69% so as to render the final antioxidant containing distilled ethanol product 28. In preferred embodiments the antioxidant-rich ethanol product 26 may be diluted to 40% alcohol concentration, the standard alcohol concentration of commercially available vodkas or hard alcoholic beverage products, so as to render the final antioxidant containing distilled ethanol product 28. Accordingly, in the instantly disclosed process, stillage is not required or utilized to reintroduce antioxidants back into a distilled ethanol product to render an antioxidant-rich ethanol product.

Therefore, with reference to FIG. 1 and in particular the hashed box noted at 30, and in accordance with in preferred embodiments, the once the sliced and/or ground frozen plant matter following 18 has been subjected to the distilled input ethanol product 12 for extraction of the antioxidants to obtain the antioxidant-rich ethanol fluid 20 through to a bottling step of the final antioxidant containing distilled ethanol product 28, it is preferable, in some embodiments, to limit exposure of the ethanol containing antioxidants to oxygen.

Furthermore, in some embodiments, it is preferable to conduct the process in a temperature-controlled environment. For example, in preferred embodiments, the temperature is maintained at about 14° C. and in an environment which limits exposure to light in order to retain, as much as possible, the antioxidant capacity of the extractable and extracted antioxidants. For example, in some embodiments during the ethanolic antioxidant extraction, the frozen plant material and the distilled input ethanol product are maintained at a temperature of from about 10° C. to about 20° C., and in preferred embodiments at about 14° C.

As antioxidants are susceptible to being rendered ineffective by higher pH levels, a low pH during the extraction step at 18 of the antioxidants by the distilled input ethanol is preferred. Accordingly, in some embodiments, it may be desirable to adjust the pH of the distilled input ethanol product 12 prior to the ethanolic extraction of the antioxidants from the washed and frozen plant material 16. For example, the pH of the distilled input ethanol product 12 may be adjusted, if required, to be between from about pH 3.0 to about pH 6.0. In preferred embodiments, the pH of the distilled input ethanol product 12 is adjusted (if required) and maintained at about 4.5. A pH of 4.5 has been determined to provide a desired balance of flavor and antioxidant extraction conditions. The pH may be adjusted using suitable bases or acids as required, as would be known by one of skill in the art.

The combination of low temperatures, low light and low pH levels during extraction in some embodiments aids to extract the antioxidants and/or anthocyanins, which ultimately remain in the antioxidant-rich ethanol product 26, with minimum degradation. Accordingly, the antioxidant-rich ethanol product 26 and any final antioxidant containing distilled ethanol product 28 may also have a colouring provided by the antioxidants and/or anthocyanins contained therein.

Continuing with reference to FIG. 1, the remnant solid plant matter 32, which is filtered at 22, is collected for use in producing a distilled ethanol. The fruit, grain and/or vegetable matter that was used in the ethanolic extraction to render the antioxidant-rich ethanol fluid 20 and from which the antioxidants have been extracted is then used in the production of ethanol which is then subsequently used as the distilled input ethanol product 12 in future antioxidant ethanol extractions. For example, the remnant solid plant matter 32, filtered from the antioxidant-rich ethanol fluid 20, is cooked so as to gelatinize starches which are present therein. In some embodiments, the remnant solid plant matter 32 may be cooked in a pressure cooker with or without additional water being added so as to gelatinize the starches present. The remnant solid plant matter 32 which has been cooked so as to gelantize the starches is subjected to one or both of an acid or enzyme treatment to promote saccharification of the starches and form a mash 34. Yeast is then added to the mash 34 to form a beer 36 and the sugars resultant from the saccharification are allowed to ferment into alcohols. The beer 36 is then distilled to obtain substantially pure ethanol 38, for example, about a 95% ethanol liquid which is then used as the distilled input ethanol product 12 in future antioxidant ethanol extractions. In some embodiments, the beer 36 may also be membrane filtered to obtain the substantially pure ethanol 38. Accordingly the obtained substantially pure ethanol 38 is then utilized as the distilled input ethanol product 12 and the process is thus cyclical. In other words, a batch of ethanol is used to extract antioxidants from suitable plant material in a first batch and then the plant material having the antioxidants extracted therefrom is used to produce a second batch of ethanol, which in turn is used to extract the antioxidant from a subsequent batch of suitable plant material. Thus, a generated batch of ethanol is invested to extract antioxidants from a batch of plant materials containing antioxidants and once the antioxidants have been extracted, the plant material is then used to generate a subsequent batch of ethanol.

Example 1

Various varieties of potatoes were tested to determine the antioxidant values which may be achieved in a diluted distilled alcohol product. Briefly, in this testing the potatoes were cooked in the absence of water in a pressure cooker with the skins on. The yielded solids content of the pressure-cooked potatoes is presented at Table 1. The cooked potatoes where ground and incorporated as part of a mash which included the enzyme pretreatment to yield fermentable sugars for a period of 24-hours. Once the mash had been pretreated with enzymes, yeast was added to the mash to form a beer and allowed to ferment for 48-hours. In Table 2 the results of the percent components are presented for various varieties of potatoes and amounts of water added to the mash as tested following enzyme pretreatment and following the yeast fermentation stage. Generally, it can be seen that the more water that is added to the mash results in a lower alcohol concentration in the beer, which is correlated with lower glucose concentrations in the mash resultant from the enzyme treatment.

TABLE 1

Analysis of Moisture Content in Raw and Cooked Potatoes

| Potato Variety | Raw (% moisture) | Cooked (boiling water) (% moisture) | Cooked (Pressure cooker) (% moisture) |
|---|---|---|---|
| Adirondack Blue | 79.84 | 79.59 | 78.96 |
| Adirondack Red | 81.40 | 83.59 | 83.58 |
| Goldrush | 79.98 | 81.79 | |
| Red Pontiac | 82.34 | 82.40 | |
| All Blue | 80.90 | 79.50 | |
| Yukon Gold | 78.30 | 79.34 | |

TABLE 2

Production of Potato Beer for Vodka Distillation

| Potato Variety + Enzymes | 24 hr Enzyme pretreatment | | | | 48 hr Yeast fermentation | | | | |
|---|---|---|---|---|---|---|---|---|---|
| | DP4+ | DP3 | Maltose | Glucose | DP4+ | DP3 | Maltose | Glucose | Ethanol |
| Adirondack Blue | 2.981 | 0 | 0.325 | 16.391 | 1.382 | 0 | 0 | 0 | 9.251 |
| Adirondack Blue + no water | 1.385 | 0 | 0 | 16.025 | 0 | 0 | 0 | 0 | 8.557 |
| Adirondack Blue + 25% water | 0.914 | 0 | 0 | 12.168 | 0 | 0 | 0 | 0 | 6.129 |
| Adirondack Blue + 50% water | 0.54 | 0 | 0 | 8.034 | 0 | 0 | 0 | 0 | 3.873 |
| Adirondack Red + no water | 0.895 | 0 | 0 | 12.501 | 0 | 0 | 0 | 0.121 | 6.139 |

TABLE 2-continued

Production of Potato Beer for Vodka Distillation

| Potato Variety + Enzymes | 24 hr Enzyme pretreatment | | | | 48 hr Yeast fermentation | | | | |
|---|---|---|---|---|---|---|---|---|---|
| | DP4+ | DP3 | Maltose | Glucose | DP4+ | DP3 | Maltose | Glucose | Ethanol |
| Adirondack Red 25% water | 0.631 | 0 | 0 | 9.118 | 0 | 0 | 0 | 0 | 4.354 |
| Adirondack Red 50% water | 0.499 | 0 | 0 | 6.249 | 0 | 0 | 0 | 0 | 2.74 |

Table 3 displays the Fermentable Amino Nitrogen (FAN) content of various varieties of potatoes. Cooking the potatoes in a pressure cooker resulted in higher FAN concentrations. Higher FAN concentrations improve fermentation by providing nitrogen that can be taken up by the yeast during fermentation and used by the yeast for the synthesis of proteins and other cellular compounds. Higher levels of FAN concentration improves yeast cell growth and multiplication, which in turn leads to better fermentation performance.

TABLE 3

FAN Analysis of Raw and Cooked Potatoes

| Sample | FAN (mg/L) RAW | FAN (mg/L) COOKED |
|---|---|---|
| Adirondack Blue | 1351 | *1103 |
| Adirondack Red | 1188 | *2000 |
| Goldrush | 1246 | 609 |
| Red #2 | 1272 | 859 |
| All Blue | 1185 | 621 |
| Yukon Gold | 1643 | 548 |

Interestingly, the darker pigmented potato varieties, those having higher levels of anthocyanins show comparatively higher FAN concentrations following cooking and therefore the yeast may provide a more efficient fermentation of the sugars in a beer using these varieties.

Following fermentation for 48-hours, the potato beer was distilled to 95% and collected.

Example 2

Following the distillation to 95% ethanol of the potato beer, analysis of the resultant vodka indicated that the distilled ethanol product contained virtually no antioxidants; returning an antioxidant value of about 0.005 for both the Adirondack Red potato and Adirondack Blue potato varieties. Accordingly, as shown below in Table 4, antioxidants present in the beer are not carried through the distillation process to the final distilled ethanol product.

Example 3

Antioxidants remain in the solids and water-soluble compounds found in the stillage remaining from the distillation process. Accordingly, in one test, the 95% distilled ethanol product was diluted to 40% (normal concentration of vodka) with the stillage. This provided a distilled ethanol with an antioxidant value of about 1.0, slightly less than the original potato (about 20% less). Furthermore, the product was a coloured product. This modified distillation method using the antioxidant-rich stillage as a diluent provided an antioxidant containing distilled ethanol product, however, the product of this method had several "off-flavourings" and was deemed to be a low-quality product having included therein undesirable components resultant from the fermentation process. Accordingly, in order to remove the off-flavourings, membrane filtration was proposed, however membrane filtration is an expensive and time-consuming process.

TABLE 4

Antioxidant Analysis of Potatoes and Potato Vodka

| Source | Antioxidant Value |
|---|---|
| Adirondack Red Raw | 1.1 |
| Adirondack Blue Raw | 1.4 |
| Adirondack Red Fermented (beer) | 1.4 |
| Adirondack Blue Fermentated (beer) | 1.3 |
| Ethanol Distilled from Adirondack Red Beer | 0.005 |
| Ethanol Distilled from Adirondack Blue Beer | 0.005 |
| Adirondack Red Centrifuged Liquid at the end of fermentation (solids removed) | 1.5 |
| Adirondack Blue Centrifuged Liquid at the end of fermentation (solids removed) | 1.4 |
| Adirondack Red Stillage Remaining After Distillation (removal of ethanol) | 1.6 |
| Adirondack Blue Stillage Remaining After Distillation (removal of ethanol) | 1.3 |
| Adirondack Red Stillage Dehydrated by Evaporation of Water (concentration) | 3.2 |
| Adirondack Blue Stillage Dehydrated by Evaporation of Water (concentration) | 2.8 |
| 95% Ethanol diluted to 40% with Adirondack Red Concentrated Stillage | 0.9 |
| 95% Ethanol diluted to 40% with Adirondack Blue Concentrated Stillage | 0.7 |

Example 4

In order to address the off-flavourings noted above with respect to the method of producing an antioxidant containing distilled alcohol product made by diluting the distilled ethanol with stillage so as to reintroduce the antioxidants, another method was developed. Surprisingly, the resultant product was rich in antioxidants and was devoid of off-flavourings. As well, the newly developed method also conferred a colouring from the plant matter to the antioxidant containing distilled alcohol product.

In the instantly disclosed method, 95% ethanol was produced via a process as outlined above. For example, Adirondack potatoes possessing high levels of antioxidants, were fermented to yield potato beer, the potato beer was then distilled by conventional methods to 95% ethanol. A second batch of antioxidant-rich potatoes was washed to remove debris and surface contaminants, then frozen and cut. The antioxidants were then extracted from the second batch of frozen and cut potatoes using 95% ethanol produced in an earlier cycle. The antioxidant-enriched ethanol was then filtered to remove the solids of the second batch of potatoes, now substantially devoid of antioxidants, and diluted to vodka standards; for example, diluted with water to a 40% alcohol concentration. Utilizing this instantly disclosed method, the obtained antioxidant-enriched ethanol was shown to have an antioxidant content of from about 150 ppm to about 200 ppm. However, other concentrations of antioxidants may be obtainable. Once diluted, the antioxidant containing distilled alcohol product could be bottled for distribution.

The filter-recovered ethanol-washed potato solids, substantially devoid of antioxidants, were then cooked and pre-treated for saccharification, either by enzyme or acid treatment or both, then fermented via yeast and used to produce 95% ethanol. The non-antioxidant containing stillage was then disposed of as waste. This next batch of 95% distilled ethanol was used to extract antioxidants from a subsequent batch of antioxidant-rich frozen and cut potatoes. Therefore, the fermented mash according to this method is distilled to generate 95% ethanol to be invested in the antioxidant extraction step of another batch of antioxidant rich potatoes, or other antioxidant bearing plant matter which is suitable to produce alcohol therefrom. Accordingly, the instantly disclosed process is cyclical and the stillage is not used to reintroduce antioxidants back into the distilled ethanol product.

It is to be understood that the above description it is intended to be illustrative, and not restrictive. Many other embodiments will be apparent to those skilled in the art, upon reviewing the above description. The scope of the invention should, therefore, be determined with reference to the appended claims, along with the full scope of equivalents to which such claims are entitled.

Although the present invention has been described with reference to specific exemplary embodiments, it will be evident that various modifications and changes may be made to these embodiments without departing from the broader spirit and scope of the disclosed subject matter as defined by the appended claims.

What is claimed is:

1. An ethanolically-extracted antioxidant containing distilled ethanol product produced by:
    freezing antioxidant containing plant matter of a given plant variety, suitable for use in the production of ethanol, to render a frozen plant material;
    subjecting the frozen plant material to a volume of a distilled input ethanol product previously produced from plant matter of the given plant variety so as to ethanolically extract antioxidants from the frozen plant material and render an antioxidant-rich ethanol fluid mixture having therein remnant solid plant matter;
    separating the remnant solid plant matter from the antioxidant-rich ethanol fluid mixture so as to obtain said antioxidant containing distilled ethanol product; and
    producing a subsequent distilled ethanol product from said remnant solid plant matter; the subsequent distilled ethanol product being used as the distilled input ethanol product in subsequent cycles for producing at least a further volume of said antioxidant containing distilled ethanol product;
    wherein the given plant variety is Adirondack Blue potatoes, Adirondack Red potatoes or a combination of Adirondack Blue potatoes and Adirondack Red potatoes.

2. The ethanolically-extracted antioxidant containing distilled ethanol product as defined in claim 1, wherein the distilled ethanol product has an antioxidant concentration of from about 150 ppm to about 200 ppm.

3. A comestible ethanolically-extracted antioxidant containing distilled ethanol product comprising at least an antioxidant component and an ethanol component;
    said antioxidant component being ethanolically extracted from a first frozen plant matter batch using a first distilled input ethanol product to render an antioxidant-rich ethanol fluid mixture having therein remnant solid plant matter, wherein the first frozen plant matter batch comprises plant matter of a given plant variety and the first distilled input ethanol product is previously-produced from plant matter of the given plant variety;
    the remnant solid plant matter subsequently being separated from said antioxidant-rich ethanol fluid so as to yield said antioxidant containing distilled ethanol product; and
    said remnant solid plant matter being used to produce a second distilled input ethanol product which is subsequently used to ethanolically extract antioxidants from a second frozen plant matter batch;
    wherein the given plant variety is Adirondack Blue potatoes, Adirondack Red potatoes or a combination of Adirondack Blue potatoes and Adirondack Red potatoes.

4. The comestible ethanolically-extracted antioxidant containing distilled ethanol product as defined in claim 3, wherein the antioxidant component comprises anthocyanins.

5. The comestible ethanolically-extracted antioxidant containing distilled ethanol product as defined in claim 3, wherein the ethanol is distilled from a beer using sugars derived from potatoes.

6. The comestible ethanolically-extracted antioxidant containing distilled ethanol product as defined in claim 3, wherein said remnant solid plant matter is substantially devoid of antioxidants.

7. The comestible ethanolically-extracted antioxidant containing distilled ethanol product as defined in claim 3, wherein the antioxidant component is in a concentration of from about 150 ppm to about 200 ppm.

8. A comestible ethanolically-extracted antioxidant containing distilled ethanol product comprising at least an antioxidant component and an ethanol component; wherein the antioxidant component is extracted from at least one of Adirondack Blue potatoes or Adirondack Red potatoes using the ethanol component and wherein the ethanol component is produced from said at least one of Adirondack Blue potatoes or Adirondack Red potatoes.

9. The comestible ethanolically-extracted antioxidant containing distilled ethanol product according to claim 8, wherein the antioxidant component comprises anthocyanins.

10. The comestible ethanolically-extracted antioxidant containing distilled ethanol product according to claim 8, wherein the antioxidant component is in a concentration of from about 150 ppm to about 200 ppm.

* * * * *